United States Patent

Ledelec et al.

[11] 4,447,438
[45] * May 8, 1984

[54] DOPAMINERGIC STIMULATING PIPERIDIN-3-YL-INDOLES

[75] Inventors: Lucien Ledelec, Le Raincy; Jacques Guillaume, Le Pre Saint Gervais; Claude Dumont, Nogent sur Marne, all of France

[73] Assignee: Roussel Uclaf, Paris, France

[*] Notice: The portion of the term of this patent subsequent to Mar. 6, 2001 has been disclaimed.

[21] Appl. No.: 395,644

[22] Filed: Jul. 6, 1982

[30] Foreign Application Priority Data

Jul. 24, 1981 [FR] France .................. 81 14428

[51] Int. Cl.³ .................. A01K 31/445; C07D 401/04
[52] U.S. Cl. .................. 424/267; 546/201
[58] Field of Search .................. 546/201; 424/267

[56] References Cited

U.S. PATENT DOCUMENTS 4,196,209  4/1980  Dumont et al. .................. 546/201 X
4,332,808  6/1982  Guillaume et al. .................. 546/201 X Primary Examiner—Richard A. Schwartz
Attorney, Agent, or Firm—Muserlian, Bierman, Bierman & Peroff

[57] ABSTRACT

Novel piperidin-3-yl-indoles of the formula

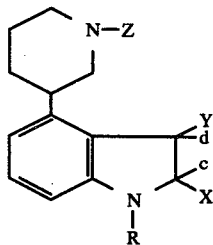

wherein R is selected from the group consisting of hydrogen, alkyl of 1 to 8 carbon atoms and aralkyl of 7 to 12 carbon atoms, X is selected from the group consisting of hydrogen, halogen and alkyl of 1 to 8 carbon atoms or with c is =O, Y is alkyl of 1 to 8 carbon atoms, c and d form a carbon-carbon bond or c with X is =O and d is hydrogen, Z is selected from the group consisting of hydrogen, alkyl of 1 to 8 carbon atoms, hydroxyalkyl of 2 to 8 carbon atoms, cycloalkylalkyl of 4 to 12 carbon atoms, alkenyl and alkynyl of 3 to 8 carbon atoms, aryloxyalkyl of 7 to 12 carbon atoms and aralkyl of 7 to 12 carbon atoms optionally substituted with at least one member of the group consisting of halogen, alkoxy and alkyl of 1 to 4 carbon atoms, —OH, —CF₃, —OCF₃, —NO₂ and —NH₂ and their non-toxic, pharmaceutically acceptable acid addition salts possessing remarkable dopaminergic stimulating properties and antianoxic properties and their preparation.

10 Claims, No Drawings

DOPAMINERGIC STIMULATING PIPERIDIN-3-YL-INDOLES

STATE OF THE ART

Copending commonly assigned U.S. patent application Ser. No. 154,507 filed May 29, 1980, now abandoned in favor of Continuation-in Part application Ser. No. 221,927 filed Dec. 31, 1980, now U.S. Pat. No. 4,332,808 describes related indoles with dopaminergic stimulating activity.

OBJECTS OF THE INVENTION

It is an object of the invention to provide the novel indoles of formula I and their non-toxic, pharmaceutically acceptable acid addition salts and a process for their preparation.

It is another object of the invention to provide novel dopaminergic stimulating compositions and to provide a novel method of inducing dopaminergic stimulating activity in warm-blooded animals.

These and other objects and advantages of the invention will become obvious from the following detailed description.

THE INVENTION

The novel compounds of the invention are selected from the group consisting of piperidin-3-yl-indoles of the formula

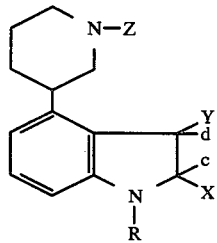

I wherein R is selected from the group consisting of hydrogen, alkyl of 1 to 8 carbon atoms and aralkyl of 7 to 12 carbon atoms, X is selected from the group consisting of hydrogen, halogen and alkyl of 1 to 8 carbon atoms or with c is =0, Y is alkyl of 1 to 8 carbon atoms, c and d form a carbon-carbon bond or c with X is =0 and d is hydrogen, Z is selected from the group consisting of hydrogen, alkyl of 1 to 8 carbon atoms, hydroxyalkyl of 2 to 8 carbon atoms, cycloalkylalkyl of 4 to 12 carbon atoms, alkenyl and alkynyl of 3 to 8 carbon atoms, aryloxyalkyl of 7 to 12 carbon atoms and aralkyl of 7 to 12 carbon atoms optionally substituted with at least one member of the group consisting of halogen, alkoxy and alkyl of 1 to 4 carbon atoms, —OH, —CF₃, —OCF₃. —NO₂ and —NH₂ and their non-toxic, pharmaceutically acceptable acid addition salts.

Examples of suitable acids for the non-toxic, pharmaceutically acceptable acid addition salts are inorganic acids such as hydrochloric acid, hydrobromic acid, nitric acid, sulfuric acid and phosphoric acid and organic acids such as acetic acid, propionic acid, formic acid, benzoic acid, maleic acid, fumaric acid, succinic acid, tartaric acid, citric acid, oxalic acid, glyoxylic acid, aspartic acid, alkanesulfonic acids such as methanesulfonic acid and arylsulfonic acids such as benzenesulfonic acid.

Examples of R are hydrogen, alkyl of 1 to 8 carbon atoms such as methyl, ethyl, propyl, isopropyl, butyl, isobutyl and n-pentyl and aralkyl of 7 to 12 carbon atoms especially benzyl. Examples of X and Y as alkyl of 1 to 8 carbon atoms are preferably alkyl of 1 to 4 carbon atoms such as methyl, ethyl, n-propyl or n-butyl and X may also be hydrogen or halogen such as chlorine or bromine.

Examples of Z are hydrogen, alkyl and hydroxyalkyl such as methyl, ethyl, n-propyl, isopropyl, n-butyl, isobutyl, n-pentyl, n-hexyl, hydroxyethyl, hydroxy-n-propyl, hydroxyisopropyl, hydroxy-n-butyl, hydroxyisobutyl, hydroxy-n-pentyl and hydroxy-n-hexyl, aryloxyalkyl such as phenoxyethyl and phenoxypropyl and aralkyl such as benzyl or phenethyl optionally substituted with at least one halogen such as chlorine or bromine or alkyl or alkoxy such as methyl, ethyl, methoxy and ethoxy or cycloalkylalkyl such as cyclopropylmethyl, cyclopropylethyl and cyclopropyl-n-propyl, alkenyl such as allyl and alkynyl such as propargyl.

Examples of preferred compounds of the invention are compounds of formula I wherein X is hydrogen or halogen, those wherein X and c are =0 and those wherein Y is methyl and those wherein Z is alkyl of 1 to 8 carbon atoms and their non-toxic, pharmaceutically acceptable acid addition salts. Especially preferred are 3-methyl-4-(piperidin-3-yl)-indole and 1a-1,3-dihydro-3-methyl-4-(piperidin-3-yl)-2H-indole-2-one and their non-toxic, pharmaceutically acceptable acid addition salts.

The novel process of the invention for the preparation of the compounds of formula I comprises reacting a compound of the formula

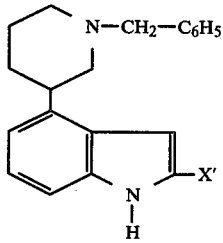

II wherein X' is selected from the group consisting of hydrogen and alkyl of 1 to 8 carbon atoms with an alkylation agent to obtain a compound of the formula

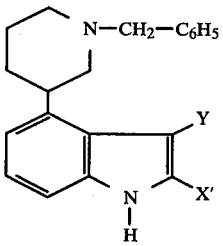

I_A wherein X' and Y have the above definitions and either recovering the same and optionally salifying the same or reacting the latter with a halogenation agent when X' is hydrogen to obtain a compound of the formula

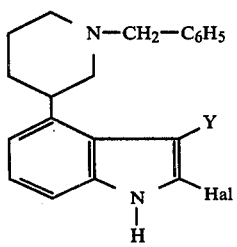

I_B wherein Hal is halogen which may be isolated or reacting a compound of formula I_A with a halide of the formula Hal_1—R'    III wherein Hal_1 is chlorine, bromine or iodine and R' is R other than hydrogen to obtain a compound of the formula

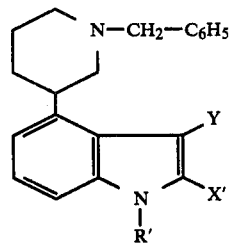

I_C which may be recovered and optionally salified or reacted with a halogenation agent when X' is hydrogen to obtain a compound of the formula

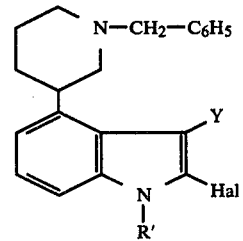

I_D which may be recovered or the compounds of formula I_A and I_C may be reacted with an agent to cleave the benzyl group from the piperidinyl nitrogen atom to obtain a compound of the formula

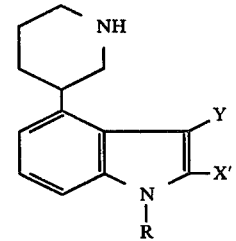

I_E which may be isolated and optionally salified or reacted with a halogenation agent when X' is hydrogen to obtain a compound of the formula

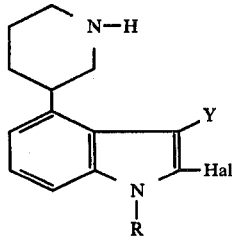

I_F which may be isolated or reacting a compound of formula I_E with a reactant to introduce Z' which is Z other than hydrogen to obtain a compound of the formula

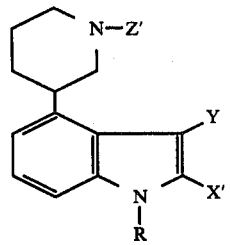

I_G which may be isolated and optionally salified or reacted with a halogenation agent when X' is hydrogen to obtain a compound of the formula

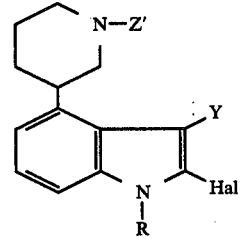

I_H which may be isolated or reacting the compound of formula I_E with an oxidizing agent when X' is hydrogen to obtain a compound of the formula

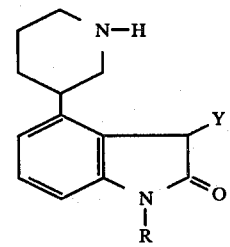

I_I which may be isolated and optionally salified or reacted with a reactant capable of introducing Z' to obtain a compound of the formula

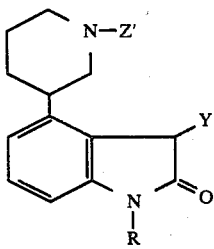

which may be isolated and optionally salified.

The alkylation of the compound of formula II may be effected by the Mannich reaction or with the aid of a Vilsmeir-Haack formylation, especially with dimethylformamide and phosphorus oxychloride followed by reduction of the formyl derivative to obtain the methyl derivative. To obtain higher homologs, the formyl derivative may be reacted with a phosphorane of the formula $(C_6H_5)_3 P=CH-Y'$ wherein $Y'$ is hydrogen or alkyl of 1 to 6 carbon atoms and hydrogenating the resulting alkenyl derivative.

The reaction of the compound of formula $I_A$ with the halide of formula III is preferably effected in the presence of an acid binding agent such as an alkali metal carbonate or hydroxide such as sodium hydroxide, sodium carbonate, potassium hydroxide or potassium carbonate or tertiary amines. The halide of formula III is preferably the iodide. The cleavage agent to remove the benzyl group from the piperidinyl nitrogen atom is preferably hydrogen in the presence of a catalyst such as palladium.

When the derivative of formula II is the methyl derivative, it is advantages to effect the Mannich reaction and then the cleavage of the benzyl occurs at the same time as the amine of the aminomethyl group by hydrogenolysis.

The introduction of the $Z'$ group is preferably realized with a halide of the formula Hal-$Z'$ wherein $Z'$ and Hal have the above definition under the conditions used for the halide of formula III.

The halogenation of the compounds of formulae $I_A$, $I_C$, $I_E$ or $I_G$ may be effected with a bromine complex or pyridine of the formula

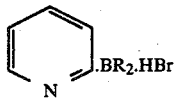

when the halogen is bromine or with a N-halosuccinimide, preferably N-bromo-succinimide or N-chlorosuccinimide. The preferred oxidation agent is a mixture of concentrated hydrochloric acid and dimethylsulfoxide.

In a variation of the process of the invention to prepare a compound of formula I wherein X and c form =O, a compound of formula $I_G$ wherein $X'$ is hydrogen may be reacted with an oxidation agent as described above to form the compound of formula $I_J$.

In another variation of the process of the invention to form a compound of formula I wherein X and c form =O, a compound of formula $I_B$, $I_D$, $I_F$ or $I_H$ is subjected to hydrolysis, preferably with a mineral acid such as hydrochloric acid to obtain the desired compound.

The compounds of formula I have a basic character and the acid addition salts may be prepared by reacting approximately stoichiometric amounts of the compound of formula I and an organic or inorganic acid and the salts may be formed without isolating the base. The compounds of formula I with a halogen in the 2-position of the indole are unstable in acid conditions so their addition salts are not formed.

The dopaminergic stimulating and antianoxic compositions of the invention are comprised of a dopaminergic stimulating and antianoxically effective amount of at least one compound of formula I and their non-toxic, pharmaceutically acceptable acid addition salts and an inert pharmaceutical carrier or excipient. The compositions may be in the form of tablets, dragees, gelules, granules, suppositories and injectable solutions or suspensions.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants or emulsifiers and preservatives.

The compositions are useful for the treatment of numerous maladies or diverse pathological disorders such as for the treatment of hypersecretion of prolactin by antehypophysis and for the treatment of hypogonadism in the male or female as well as for the treatment of Parkinson disease and in the treatment of post-encephalitic parkinsonian syndromes. They are also useful for the treatment of cerebral senescence and geriatry.

Examples of preferred compositions of the invention are those containing compounds of formula I wherein X is hydrogen or halogen, those wherein X and c are =O and those wherein Y is methyl and those wherein Z is hydrogen or alkyl of 1 to 8 carbon atoms and their non-toxic, pharmaceutically acceptable acid addition salts. Especially preferred are 3-methyl-4-(piperidin-3-yl) 1H-indole and 1,3-dihydro-3-methyl-4-(piperidin-3-yl)-2H-indole-2-one and their non-toxic, pharmaceutically acceptable acid addition salts.

The novel method of the invention of inducing dopaminergic stimulating and antianoxic activity in warm-blooded animals, including humans, comprises administering to warm-blooded animals a dopaminergic stimulating and antianoxically effective amount of at least one compound of formula I and their non-toxic, pharmaceutically acceptable acid addition salts. The compounds may be administered orally, rectally or parenterally and the daily dose will depend upon the condition being treated and the specific compound used but is usually between 0.1 to 20 mg/kg. The compound of Example 2 may be orally administered at a daily dose of 0.1 to 1.5 mg/kg for the treatment of Parkinson disease, for example.

The compounds of formulae II and III are known and may be prepared by the process of French Pat. No. 2,458,549 or European patent application No. 0021,924.

In the following examples there are described several preferred embodiments to illustrate the invention. However, it is to be understood that the invention is not intended to be limited to the specific embodiments.

EXAMPLE 1

3-methyl-4-(piperidin-3-yl)-1H-indole hydrochloride

STEP A: N,N-dimethyl-4-(1-benzyl-piperidin-3-yl)-1H-indole-3-methanamine 2.5 ml of acetic acid and then 1.4 ml of an aqueous 40% formaldehyde solution were slowly added with stirring at 0° to 5° C. under an inert atmosphere to 2.5 ml of an aqueous 35% dimethylamine solution and then a solution of 5.5 g of 4-(1-benzyl-piperidin-3-yl)-1H-indole in 25 ml of acetic acid was added to the mixture. The mixture was stirred at room temperature for 90 minutes and was then diluted with water. Sodium hydroxide was added to the mixture to make it basic and the mixture was filtered. The recovered product was washed with water, dried under reduced pressure and crystallized from benzene to obtain 3 g of N,N-dimethyl-4-(1-benzyl-piperidin-3-yl)-1H-indole-3-methanamine melting at ≃150° C.

STEP B: 3-methyl-4-(piperidin-3-yl)-1H-indole hydrochloride

A stirred mixture of 4.3 g of the product of Step A, 1.5 g of 10% palladized carbon and 300 ml of methanol was hydrogenated at 40° C. for one hour after which another 1.5 g of 10% palladized carbon were added. The hydrogenation was continued for another hour and the mixture was filtered. The filtrate was evaporated to dryness under reduced pressure at 50° C. to obtain 2.5 g of 3-methyl-4-(piperidin-3-yl)-1H-indole melting at 150° C. The said product was dissolved in 250 ml of ethyl acetate and then a solution of hydrogen chloride in ethyl acetate was added thereto at 0° to 5° C. until the mixture was acidic. The mixture was filtered and the product was washed with ethyl acetate, dried at 50° C. under reduced pressure and was crystallized from isopropanol to obtain 2.4 g of 3-methyl-4-(piperidin-3-yl)-1H-indole hydrochloride melting at 280° C.

Analysis: $C_{14}H_{19}N_2Cl$: molecular weight=250.773. Calculated: %C 67.05, %H 7.64, %N 11.17, %Cl 14.14. Found: %C 66.7, %H 7.6, %N 11.1, %Cl 14.1.

EXAMPLE 2

1,3-dihydro-3-methyl-4-(piperidin-3-yl)-2H-indole-2-one

A mixture of 5 g of the hydrochloride of Example 1, 14 ml of dimethylformamide and 32 ml of 22° Be hydrochloric acid was stirred at room temperature under an inert atmosphere for 30 minutes and was then diluted with water. Sodium hydroxide was added to the mixture until the pH was basic and the mixture was extracted with ethyl acetate. The organic phase was washed with water and then with aqueous sodium hydroxide solution, was dried and evaporated to dryness at 40° C. under reduced pressure. The residue was chromatographed over silica gel and was eluted with a 6-3-1 chloroform-acet-one-triethylamine mixture to obtain 3.1 g of 1,3-dihydro-3-methyl-4-(piperidin-3-yl)-2H-indole-2-one with a Rf=0.1.

UV Spectrum (ethanol): max. at 250 nm—$E_{1cm}^{1\%}=336$, $\epsilon=7700$. Max. at 280 nm—$E_{1cm}^{1\%}=58$, $\epsilon=1300$.

UV Spectrum (0.1 N NaOH in ethanol): max. at 263-264 nm—$E_{1cm}^{1\%}=352$, $\epsilon=8100$. Inflex. towards 274 nm—$E_{1cm}^{1\%}=287$. Inflex. towards 290 nm—$E_{1cm}^{1\%}$, $\epsilon=84$ IR Spectrum (chloroform): Absorption at 3440 cm$^{-1}$ (NH of

+associated); at 1715 cm$^{-1}$ (carbonyl of γ-lactam); at 1620, 1600 and 1490 cm$^{-1}$ (aromatic).

EXAMPLE 3

2-bromo-3-methyl-4-(piperidin-3-yl)-1H-indole

A mixture of 250 mg of the hydrochloride of Example 1, 10 ml of dioxane and 178 mg of N-bromosuccinide was stirred at room temperature under an inert atmosphere for 20 hours and was then poured into water. The mixture was made alkaline and was then extracted with ethyl acetate. The organic phase was dried and evaporated to dryness at 40° C. under reduced pressure. The residue was chromatographed over silica gel and was eluted with a 6-3-1 chloroform-acetone-triethylamine mixture to obtain 120 mg of 2-bromo-3-methyl-4-(piperidin-3-yl)-1H-indole. UV Spectrum (ethanol): max. at 224 nm—$E_{1cm}^{1\%}=1100$, $\epsilon=32,250$. Inflex. towards 276 nm—$E_{1cm}^{1\%}=291$. Max. at 280 nm—$E_{1cm}^{1\%}=300$, $\epsilon=8800$. Inflex. towards 289 nm—$E_{1cm}^{1\%}=244$.

EXAMPLE 4

1,3-dihydro-3-methyl-4-(piperidin-3-yl)-2H-indole-2-one

A solution of 120 mg of the product of Example 3 in N hydrochloric acid solution was stirred at room temperature for one hour and was then treated as in Example 2 to obtain 47 mg of 1,3-dihydro-3-methyl-4-(piperidin-3-yl)-2H-indole-2-one.

EXAMPLE 5

Tablets were prepared containing 15 mg of 3-methyl-4-(piperidin-3-yl)-1H-indole hydrochloride and sufficient excipient of lactose, starch, talc and magnesium stearate to obtain a final weight of 100 mg.

PHARMACOLOGICAL STUDY

A. Rotation after unilateral lesin of nigrostriatal faisceau with 6-hydroxydopamine The lesion was effected on male rats weighing about 220 g by a unilateral injection of a 2 μg/μl solution of 8 μg of 6-hydroxydopamine into the nigrostriatal dopaminergic faisceau [Ungerstedt, Acta Physiol. Scand., Vol. 82, sup. 367 (1971), p. 69-93]. In these animals, the administration of direct dopaminergic agonists such as apomorphine generally causes a rotation in the contralateral direction of the lesion side. The test compound was administered at least 5 weeks after the lesion and the animals were placed in an automatic rotometer to count the number of rotations effected by each animal in 2 directions. The compound of Example 1 at a dose of 10 mg/kg provoked 400 to 700 contralateral rotations per animal.

B. Inhibition of in vivo plasmatic prolactin

Pairs of male rats of the Sprague-Dawley strain were placed in cages and were left one week in a soundproof room at a controlled temperature of 22°±2° C. with 14 hours of artificial light and 10 hours of night. While anesthesized, a catheter was placed in the right superior vena cava of the rats and 48 hours later, the rats received intraperitoneally 5 mg/kg of reserpine then orally 5 mg/kg of the test compound. The plasmatic prolactin was measured by the radioimmunological method of Euvrard et al [Neuropharmacology, Vol. 19 (1980), p. 379] in 0.7 ml blood samples. The results expressed in the duration of inhibition of plasmatic prolactin showed that the products of Examples 1 and 2 inhibited plasmatic prolactin from about 10 and 15 hours, respectively.

C. Inhibition of prolactin secretion in rat cells in vitro

Primary cultures of anterior pituitary cells of rats were prepared by the technique of Drouin et al [Endocrinology Vol. 98 (1976), p. 1528] and after incubation for 4 hours with the test product or without (controls), the prolactin present in the medium was measured by the radio-immonological method of Euvrard et al described in test B. The $DE_{50}$ results which is the dose which inhibited by 50% the prolactin secretion as compared to the controls was 500 mmoles and 10 mmoles for the products of Examples 1 and 2, respectively.

D. Acute toxicity

The $DL_0$ dose which is the maximum dose which did not cause any deaths in 8 days was determined by oral administration of the test compounds to mice. The $DL_0$ dose for the compounds of Examples 1 and 2 were 80 and 200 mg/kg, respectively.

Various modifications of the products and processes of the invention may be made without departing from the spirit or scope thereof and it should be understood that the invention is intended to be limited only as defined in the appended claims.

What is claimed is:

1. A compound selected from the group consisting of piperidin-3-yl-indoles of the formula

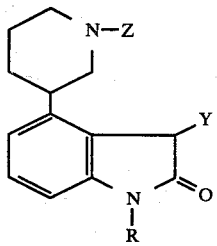

wherein R is selected from the group consisting of hydrogen, alkyl of 1 to 8 carbon atoms and aralkyl of 7 to 12 carbon atoms, Y is alkyl of 1 to 8 carbon atoms, Z is selected from the group consisting of hydrogen, alkyl of 1 to 8 carbon atoms, hydroxyalkyl of 2 to 8 carbon atoms, cycloalkylalkyl of 4 to 12 carbon atoms, alkenyl and alkynyl of 3 to 8 carbon atoms, aryloxyalkyl of 7 to 12 carbon atoms and aralkyl of 7 to 12 carbon atoms optionally substituted with at least one member of the group consisting of halogen, alkoxy and alkyl of 1 to 4 carbon atoms, —OH, —CF$_3$, —OCF$_3$, —NO$_2$ and —NH$_2$ and their non-toxic, pharmaceutically acceptable acid addition salts.

2. A compound of claim 1 wherein Y is methyl.

3. A compound of claim 1 wherein Z is hydrogen or alkyl of 1 to 8 carbon atoms.

4. A compound of claim 1 selected from the group consisting of 1,3-dihydro-3-methyl-4-(piperidin-3-yl)-2H-indole-2-one and its non-toxic, pharmaceutically acceptable acid addition salts.

5. A dopaminergic stimulating and antianoxic composition comprising a dopaminergic stimulating and antianoxically effective amount of at least one compound of claim 1 and a pharmaceutical carrier.

6. A composition of claim 5 wherein Z is hydrogen or alkyl of 1 to 8 carbon atoms.

7. A composition of claim 5 wherein the active compound is selected from the group consisting of 1,3-dihydro-3-methyl-4-(piperidin-3-yl)-2H-indole-2-one and its non-toxic, pharmaceutically acceptable acid addition salts.

8. A method of inducing dopaminergic stimulating activity in warm-blooded animals comprising administering to warm-blooded animals a dopaminergic stimulating effective amount of at least one compound of claim 1.

9. A method of claim 8 wherein Z is hydrogen or alkyl of 1 to 8 carbon atoms.

10. A method of claim 8 wherein active compound is selected from the group consisting of 1,3-dihydro-3-methyl-4-(piperidin-3-yl)-2H-indole-2-one and its non-toxic, pharmaceutically acceptable acid addition salts.

* * * * *